United States Patent [19]

Wilson

[11] Patent Number: 5,328,930
[45] Date of Patent: Jul. 12, 1994

[54] TREATMENT OF MICROSPORIDIAL AND ACANTHAMOEBA KERATOCONJUNCTIVITIS WITH TOPICAL FUMAGILLIN

[75] Inventor: Louis A. Wilson, Marietta, Ga.

[73] Assignee: Emory University, Atlanta, Ga.

[21] Appl. No.: 24,718

[22] Filed: Mar. 1, 1993

[51] Int. Cl.$^5$ ............................................. A01N 43/20
[52] U.S. Cl. .................................. 514/475; 514/912; 514/914
[58] Field of Search ........................................ 514/475

[56] References Cited

FOREIGN PATENT DOCUMENTS 325199  7/1989  European Pat. Off. .
447351  9/1991  European Pat. Off. .
286617 11/1990  Japan .

OTHER PUBLICATIONS

Rosberger D. F. et al, Cornea (1993 May) 12(3) 261-5.
Diesenhouse, M. C. et al, Am. J. Ophthalmol. (1993 Mar. 15) 115(3) 293-8.
Molnar, K et al, Dis. Aguat. Org., 2(3) 187-90 1987.
Blanshard, C., et al., "Treatment of Intestinal Microsporidiosis with Albendazole in Patients with AIDS," *AIDS*, vol. 6 (1992) pp. 311-313.
Bryan, R. T., et al., "Microsporidia: Opportunistic Pathogens in Patients with AIDS," *Progress in Clinical Parasitology*, vol. 2, (1991) pp. 1-26.
Current, W. L., et al., "Cryptosporidiosis and Microsporidiosis," *Enteric Infection: Mechanisms, Manifestations and Management*, Chapman and Hall Medical: London (1989) pp. 223-249.
Davis, R. M., et al., "Corneal Microsporidiosis," *Ophthalmology* vol. 97, No. 7 (Jul. 1990) pp. 963-957.
Didier, E. S., et al., "Isolation and Characterization of a New Human Microsporidian, Encephalitozoon hellem (n, sp.), from Three AIDS Patients with Keratoconjunctivitis," *J. Infectious Diseases*, vol. 163 (Mar. 1991) pp. 617-621.
Edlind, T. D., et al., "Activity of the Anthelmintic Benzimidazoles against *Giardia lamblia* in Vitro," *J. Infectious Diseases*, vol. 162 (Dec. 1990) pp. 1408-1411.
Friedberg, D. N., "Microsporidial Keratoconjunctivitis in Acquired Immunodeficiency Syndrome," *Arch. Ophthalmology*, vol. 108, No. 1 (Jan. 1990) pp. 504-508.
Hartwig, A., et al., "Nucleic Acids in Intestine of *Apis mellifica* Infected with *Nosema apis* and Treated with Fumagillin DCH: Cytochemical and Autoradiolographic Studies," *J. Invertebrate Pathology*, vol. 18 (1971) pp. 331-336.
Jaronski, S. T., "Cytochemical Evidence for RNA Synthesis Inhibition by Fumagillin," *J. Antibiotics*, vol. 25, No. 6 (Jun. 1972) pp. 327-331.
Killough, J. H., "The Treatment of Amebiasis with Fumagillin," *Science* vol. 115, pp. 71-72 1952.
Kurtti, T. J., et al., "The Rate of Development of a Microsporidan in Moth Cell Culture," *J. Invertebrate Pathology*, vol. 29, No. 2 (Mar. 1977) pp. 127-132.
Larkin, D. F. P., et al., "Treatment of *Acanthamoeba* Keratitis with Polyhexamethylene Biguanide," *Ophthalmology*, vol. 99, No. 2 (Feb. 1992) pp. 185-191.
Lowder, C. Y., et al., "Microsporidia Infection of the Cornea in a Man Seropositive for Human Immunodeficiency Virus," *American Journal of Ophthalmology*, vol. 109 (Feb. 15, 1990) pp. 242-245.
McCowen, M. C., et al., "Fumagillin (H-3), a New Antibiotic with Ambicidal Properties," *Science*, vol. 113, pp. 202-203 1951.
Metcalfe, T. W., et al., "Microsporidial Keratoconjunctivitis in a Patient with AIDS," *British Journal of Ophthalmology*, vol. 76 (1992) pp. 177-178.

(List continued on next page.)

*Primary Examiner*—Paul J. Killos
*Attorney, Agent, or Firm*—Kilpatrick & Cody

[57] ABSTRACT

Methods for the treatment of Microsporidia keratoconjunctivitis and Acanthamoeba keratitis are disclosed that include the topical administration of an effective amount of fumagillin or a derivative or pharmaceutically acceptable salt thereof, in a pharmaceutically acceptable carrier or diluent.

24 Claims, No Drawings

OTHER PUBLICATIONS

Schattenkerk, J. K., et al., "Clinical Significance of Small-Intestinal Microsporidiosis in HIV-1-Infected Individuals," *The Lancet*, vol. 337, No. 8746, (Apr. 1991) pp. 895-898.

Shadduck, J. A., "Microsporidia and Human Infections," *Clinical Microbiology Reviews*, vol. 2, No. 2 (Apr. 1989) pp. 158-165.

Shadduck, J. A., et al., "Isolation of a Microsporidian from a Human Patient," *J. Infectious Diseases*, vol. 162 (Sep. 1990) pp. 773-776.

Shadduck, J. A., "Effect of Fumagillin on *in vitro* Multiplication of *Encephalitozoon cuniculi*," *J. Protozool*, vol. 27, No. 2 (1980) pp. 202-208.

Shadduck, J. A., "Human Microsporidiosis and AIDS," *Reviews of Infectious Diseases*, vol. 11, No. 2 (Mar.-Apr. 1989) pp. 203-207.

Sohi, S. S., et al., "Effect of Antimicrosporidian and Antibacterial Drugs on *Nosema disstriae* (Microsporida) Infection in *Malacosoma disstria* (Lepidoptera: Lasiocampidae) Cell Culture," *Can. J. Zool.*, vol. 57 (1979) 1222-1225.

Toguebave, B. S., et al., "Effects of Fumagillin and Benomyl on Experimental Microsporidiosis in Helithis Armigera," *Chemical Abstracts* vol. 99, No. 11 (1983) 99:83611t.

Visvesbava, G. S., et al., "Culture, Electron Microscopy, and Immunoblot Studies on a microsporidian Parasite Isolated from the Urine of a Patient with AIDS," *J. Protozoology*, vol. 38 (1991) pp. 105S-111S.

Yee, R. W., "Resolution of Microsporidial Epithelial Keratopathy in a Patient with AIDS," *Ophthalmology*, vol. 98, No. 2 (Feb. 1991) pp. 196-201.

"Microsporidian Keratoconjunctivitis in Patients with AIDS," *Morbidity and Mortality Weekly Report*, vol. 39, No. RR-3 (Mar. 1990) pp. 188-189.

Sudo, et al., "Anti-Angiogenic Action of AGM-1470, a New Synthetic Analog of Fumagillin," *Proceedings of the 82nd Annual Meeting of the American Association for Cancer Research*, Houston, Tex., vol. 32 (Mar. 1991).

TREATMENT OF MICROSPORIDIAL AND ACANTHAMOEBA KERATOCONJUNCTIVITIS WITH TOPICAL FUMAGILLIN

This invention is in the area of treatment of ocular microsporidia and acanthamoeba infections with a topical composition of fumagillin or a derivative thereof.

BACKGROUND OF THE INVENTION

Microsporidia are obligate, intracellular, spore-forming protozoan parasites that belong to the phylum Microspora, which contains approximately 80 genera and more than 700 species. They are ubiquitous in nature and have been recognized in both vertebrates and invertebrates as the cause of a disease called microsporidiosis. The parasites are characterized by the structure of their spores, which have a complex tubular extrusion mechanism used for injecting the infective material (sporoplasm) into the host cells. The parasites are important causes of disease in certain animals, including rabbits, foxes, dogs, and squirrel monkeys.

To date, only four genera of Microsporidia have been implicated as a cause of human disease: Pleistophora, Enterocytozoon, Nosema, and Encephalitozoon. Shadduck, J. A., and Greeley, E.: Microsporidia and human infections. *Clin. Micro. Rev.* 2:158, 1989. The first case of microsporidiosis in a human was diagnosed in 1959 in a nine year old Japanese boy, on the identification of Encephalitozoon spores in the cerebral spinal fluid and subsequently in the urine. The patient recovered on treatment with sulphisoxazole.

Microsporidial infections are rare in immunocompetent humans. The dramatic recent increase in human immunodeficiency viral (HIV) infections, the causative agent of acquired immunodeficiency syndrome (AIDS), has been accompanied by a dramatic increase in opportunistic infections, including Microsporidial infections, in the host.

Of the four genera of Microsporidia that are known to infect humans, only Nosema spp and Encephalitozoon spp have been noted to cause ocular infection. Cali, A., et al., Corneal microsporidiosis: Characterization and identification. *J. Protozool.* 38:215S, 1991. Microsporidial keratoconjunctivitis is often recalcitrant to topical medical therapy. Laboratory diagnosis of the disease has been made chiefly through examination of stained smears of conjunctival and corneal scrapings using transmission electron microscopy.

The species *Encephalitozoon cuniculi* (*E. cuniculi*) develops within host cells in vacuoles bounded by a membrane that is thought to be of host cell origin. Ocular *E. cuniculi* infections result in an intractable keratoconjunctivitis that has been reported only in HIV-seropositive individuals who have AIDS.

Yee, et al., reported in 1990 that an HIV-positive patient with bilateral epithelial keratopathy caused by *E. cuniculi* was not responsive to sulfa drugs, erythromycin, bacitracin, tobramycin, neomycin, polymyxin B, or fluconozole. Complaints by the patient included foreign body sensation, ocular watery discharge, redness of the eye, and later, a burning sensation and photophobia. The infection was ultimately controlled with zidovudine and itraconazole. Yee, R. W., Tio, F. O., Martinez, J. A., Held, K. S., Shadduck, J. A., and Didier, E. S.: Resolution of microsporidial epithelial keratopathy in a patient with AIDS. *Ophthalmology* 98:196, 1991. However, others have evaluated itraconazole against *E. cuniculi* and found it not significantly effective against the organism.

Friedberg, et al., reported in 1990 the case histories of three AIDS patients with bilateral coarse superficial epithelial keratitis caused by *E. cuniculi*. Symptoms included blurred vision, irritation, photophobia, and dryness. Two of the patients did not respond to a number of treatments, and the third obtained comfort and improvement in vision with sulfisoxazole, but no clinical change on ocular examination. Cunjunctival scrapings revealed the presence of numerous protozoa. Friedberg, D. N., Stenson, S. M., Orenstein, J. M., Tierno, P. M., and Charles, N. C.: Microsporidial keratoconjunctivitis in acquired immunodeficiency syndrome. *Arch. Ophthalmol.* 108:504, 1990.

Metcalf, et al., reported the case history of an AIDS patient with chronic keratoconjunctivitis also caused by *E. cuniculi*. The patient reported blurred vision and ocular discomfort. Treatment with propamidine isethionate provided temporary resolution of the infection. Metcalfe, T. W., Doran, R. M. L., Rowlands, P. L., Curry, A., and Lacey, C. J. N.: Microsporidial keratoconjunctivitis in a patient with AIDS. *Br. J. Ophthalmol.* 76:177, 1992. Others, however, have evaluated propamidine against *E. cuniculi* and found it not significantly effective against the organism.

Until recently, *E. cuniculi* was thought to be the only species within the genus Encephalitozoon to cause keratoconjunctivitis. In 1991, however, Didier, et al., reported a new Encephalitozoon species, which was designated *E. hellem*, isolated from three AIDS patients with keratoconjunctivitis. Didier, et al., *J. Infect. Dis.* 163:617, 1991.

Human ocular infection caused by members of the genus Nosema occurs in Human Immunodeficiency Virus (HIV)-seronegative as well as HIV-seropositive patients and typically results in corneal stromal ulceration both with and without antecedent trauma. Davis, et al., reported the case study of a healthy HIV-seronegative 45-year old man who developed stromal keratitis and iritis in his left eye caused by a protozoa of the Nosema genus. The patient's clinical course was characterized by progressive central discoform keratitis, and recurrent peripheral anterior stromal patchy infiltration with overlying punctate epitheliopathy, and anterior iritis. The patient was ultimately treated by keratoplasty with cryotherapy applied to the recipient edge for 360 degrees at −60 degrees centigrade before corneal trephination in an attempt to eliminate organisms in the corneal periphery.

Acanthamoeba Keratitis, which is caused by the free-living amoeba acanthamoeba, has also become recognized as a very challenging ocular infection in light of its protracted painful clinical course and frequent treatment failures. Symptoms of the infection include marked pain and photophobia with paracentral ring-shaped stromal infiltration occurring in advanced stages of the disease. Acanthamoeba keratitis was first reported in 1974 and remained a rare infection until it became associated with contact lens wear. Risk factors associated with Acanthamoeba keratitis include contaminated tap water, home-prepared saline and chemical disinfection solutions, and minor corneal injury.

In vitro tests have identified a number of compounds that may be useful in the treatment of Acanthamoeba keratitis, including propamidine isothionate, the aminoglycosides neomycin and paromomycin, and imidazole derivatives miconazole, clotrimazole, ketoconazole, and itraconazole. It has also been reported that polyhexamethylene biguanide is effective against Acanthamoeba. Larkin, et al., *Ophthalmology* 1992; 99:185-191.

In light of the increasing diagnosis of ocular Microsporidia and Acanthamoeba infections, as well as the uncomfortable and sometimes disabling effect of the diseases, it is important to have an effective treatment that is not unduly toxic to the host.

Fumagillin is an antibiotic produced by *Aspergillus fumagatus*. It has been tested for use as an antiamoebic in humans (but never marketed as such), and is currently used as an antiprotozoal in the control of Nosema apis in honey bees. Hartwig, A. and Przelecka, A.: Nucleic acids in intestine of *Apis mellifica* infected with Nosema apis and treated with fumagillin DCH: cytochemical and autoradiographic studies. *J. Invertebr. Pathol.* 18:331, 1971. Jaronski, S. T.: Cytochemical evidence for RNA synthesis inhibition by fumagillin. *J. Antibiot.* 25:327, 1972.

Shadduck reported in 1980 that fumagillin inhibits the multiplication of *E. cuniculi* in rabbit and canine cells in cell culture. Fumagillin was found to have no effect on spores or proliferative forms of the parasite in vitro. Shadduck, J. A.: Effect of fumagillin on in vitro multiplication of *Encephalitozoon cuniculi*. *J. protozool.* 27:202, 1980. The antibiotic did not reduce the number of organisms in previously infected cell cultures to zero, but prevented infection of host cells when added to the medium simultaneously with the organism. Shadduck concluded that his data suggests that fumagillin would not eliminate all viable *E. cuniculi* organisms in infected hosts, but might reduce multiplication of the parasite sufficiently to permit other host defense mechanisms to destroy remaining organisms. In a subsequent paper, Shadduck concluded that while fumagillin is effective in preventing the multiplication of *E. cuniculi* in vitro, the only available formulation is intended for use in honey bees and is toxic to humans. Further, Shadduck, in a review article subsequent to his work with fumagillin, concluded that there is no known treatment for microsporidial infections. *Review of Infectious Diseases*, Vol 11(2), 203-207, 1989.

It is an object of the present invention to provide an effective treatment for Microsporidial keratoconjunctivitis.

It is another object of the present invention to provide an effective treatment for Acanthomoeba keratoconjunctivitis.

It is a further object of the present invention to provide a topical composition that is effective against Microsporidial and Acanthamoeba keratoconjunctivitis.

SUMMARY OF THE INVENTION

Methods for the treatment of Microsporidia keratoconjunctivitis and Acanthamoeba keratitis are disclosed that include the topical administration of an effective amount of fumagillin or a derivative or pharmaceutically acceptable salt thereof, in a pharmaceutically acceptable carrier or diluent.

The discovery that fumagillin is a useful treatment against ocular parasites is surprising in light of the prior assumption that fumagillin formulations are too toxic for administration. It has now been observed that topical compositions of fumagillin are effective in vivo against these parasites, without serious side effects or toxicity.

Fumagillin or its pharmaceutically acceptable salt or derivative can be administered topically in a suspension, solution, or ointment. A typical regimen includes application of a topical solution that contains any effective amount, generally between approximately 50 μg/ml and 10 mg/ml of active compound or its salt, and more generally, between 70 μg/ml and 1 mg/ml of active material. The topical composition is applied on any appropriate periodic schedule, typically between once and four times daily. The topical composition can be continued indefinitely as necessary. Alternatively, the treatment can be stopped for a period, and then resumed as necessary on recurrence of symptoms.

DETAILED DESCRIPTION OF THE INVENTION

The term alkyl, as used herein, and unless otherwise defined, refers to $C_1$ to $C_{10}$ alkyl, specifically including but not limited to methyl, ethyl, propyl, butyl, pentyl, hexyl, isopropyl, isobutyl, sec-butyl, t-butyl, isopentyl, amyl, t-pentyl, 3-methylbutyryl, cyclopentyl, and cyclohexyl.

Methods are disclosed for the treatment of Microsporidial keratoconjunctivitis and Acanthamoeba keratitis that include the topical administration of an effective amount of fumagillin or a derivative thereof, as defined below, or a pharmaceutically acceptable salt thereof, in a pharmaceutically acceptable carrier or diluent.

The method can be used to treat Microsporidial keratoconjunctivitis that is caused by a range of microsporidial parasites, including but not limited to those caused generally by the Pleistophora, Enterocytozoon, Nosema, and Encephalitozoon genera, and specifically, those caused by *E. cuniculi*, *E. hellem*, and Nosema spp. The method can also be used to treat Acanthamoeba keratitis.

The progress of treatment can be monitored by evaluation of symptoms of the disease, or alternatively, by examination of eye scrapings for viable parasites. The scrapings can be examined with, for example, electron microscopy, light microscopy, or immunofluorescent microscopy.

I. FUMAGILLIN AND DERIVATIVES THEREOF

Fumagillin, as illustrated below, is 2,4,6,8-decatetraenedioic acid mono-[5-methoxy-4-[2-methyl-3-(3-methyl-2-butenyl)oxiranyl]-1-oxaspiro[2.5]oct-6-yl]ester. It is also referred to as 2,4,6,8-decatetraenedioic acid mono[4-(1,2-epoxy-1,5-dimethyl-4-hexenyl)-5-methoxy-1-oxaspiro[2.5]oct-6-yl]ester. It has also been referred to under the tradenames Amebacilin, Fugillin, Fumadil B, and Fumidil.

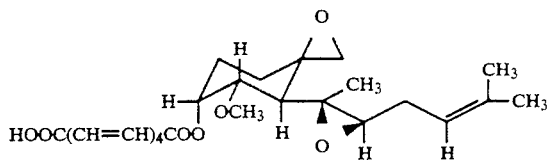

Fumagillin is a naturally secreted, water insoluble antibiotic of Aspergillus fumigatus noted to possess an inhibitory effect on intestinal protozoa including *Entamoeba hystolytica*. McCowen, M. C., Callender, M. E., and Lawlis, J. F. Jr.: Fumagillin (H-3), a new antibiotic with amebicidal properties. *Science.* 113:202, 1951; Killough, J. H., Magill, G. B., and Smith, R. C.: The treatment of amebiasis with fumagillin. *Science.* 115:71, 1952.

Fumidil B (fumagillin bicyclohexyl ammonium salt) is a water soluble form of fumagillin used commercially to control nosematosis, a microsporidial disease of honey bees caused by *Nosema apis*. Ketznelson, H. and Jamieson, C. A.: Control of nosema disease of honey bees with fumagillin. *Science*. 115:70, 1952.

Pharmaceutically acceptable derivatives of fumagillin include compounds of the formula:

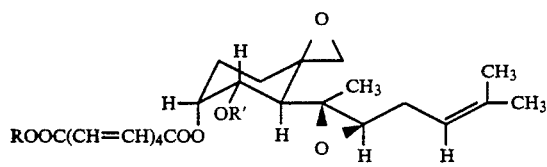

wherein:

R is hydrogen; $C_1$ to $C_{10}$ alkyl, specifically including but not limited to methyl, ethyl, propyl, butyl, pentyl, hexyl, isopropyl, isobutyl, sec-butyl, t-butyl, isopentyl, amyl, t-pentyl, 3-methylbutyryl, cyclopentyl, and cyclohexyl; or aryl, including phenyl and benzyl, optionally substituted with halogen, $C_1$ to $C_4$ alkyl or $C_1$ to $C_4$ alkoxy, or a mixture thereof; and R' is hydrogen; $C_1$ to $C_{10}$ alkyl, specifically including but not limited to methyl, ethyl, propyl, butyl, pentyl, hexyl, isopropyl, isobutyl, sec-butyl, t-butyl, isopentyl, amyl, t-pentyl, 3-methylbutyryl, cyclopentyl, and cyclohexyl; aryl including phenyl and benzyl, optionally substituted with halogen, $C_1$ to $C_4$ alkyl or $C_1$ to $C_4$ alkoxy, or a mixture thereof; or acyl. The term acyl includes C(O)R'' wherein R'' is a straight, branched, or cyclic $C_1$ to $C_{10}$ alkyl, alkoxyalkyl including methoxymethyl, aralkyl including benzyl, aryloxyalkyl such as phenoxymethyl; aryl including phenyl and benzyl optionally substituted with halogen, $C_1$ to $C_4$ alkyl or $C_1$ to $C_4$ alkoxy, or a mixture thereof; sulfonate esters such as alkyl or aralkyl sulphonyl including methanesulfonyl, the mono, di or triphosphate ester, trityl or monomethoxytrityl; trialkylsilyl (e.g. dimethyl-t-butylsilyl) or diphenylmethylsilyl. Aryl groups in the esters optimally comprise a phenyl group. The term acyl also includes hydrogen succinate, 3-chlorobenzoate, benzoyl, acetyl, pivaloyl, mesyl, propionyl, butyryl, valeryl, caproic, caprylic, capric, lauric, myristic, palmitic, stearic, and oleic. Unless otherwise specified, alkyl includes $C_1$ to $C_{10}$ straight, branched, or cyclic saturated hydrocarbons.

Modifications of the active compound can affect the bioavailability and rate of metabolism of the compound. Further, the modifications can affect the antimicrosporidial or antiacanthamoebic activity of the compound, in some cases increasing the activity over the parent compound. This can easily be assessed by preparing the derivative and testing it according to the methods described herein, or other method known to those skilled in the art.

Fumagillin or its derivative can also be administered topically as a pharmaceutically acceptable salt. For example, the parent fumagillin is relatively water insoluble, and thus, when water solubility is desired, fumagillin can be provided as a water soluble salt. As used herein, the term pharmaceutically acceptable salt refers to salts of the active compound that retain the desired biological activity of the parent compound or derivative thereof and exhibit minimal, if any, undesired toxicological effects. Base addition salts include but are not limited to those formed with polyvalent metal cations such as zinc, calcium, bismuth, barium, magnesium, aluminum, copper, cobalt, nickel, cadmium, sodium, potassium, and the like, or with an organic cation formed from N,N-dibenzylethylene-diamine, ammonium, alkylammonium, dialkylammonium, trialkylammonium, or ethylenediamine. A specific example of a water soluble version of fumagillin is Fumidil B (fumagillin bicyclohexyl ammonium salt).

II. PHARMACEUTICAL COMPOSITIONS

The active compound is included in the pharmaceutically acceptable topical carrier or diluent in an amount sufficient to deliver to a patient a therapeutically effective amount of compound to inhibit microsporidial or acanthamoebic infection in vivo, without causing serious toxic effects in the patient treated.

A preferred dose of the active compound for all of the above-mentioned conditions will be in the range between approximately 50 μg/ml and 10 mg/ml of active compound or its salt, and more generally, between 70 μg/ml and 1 mg/ml of active material. The topical composition is applied on any appropriate periodic schedule, typically between once and four times daily. The topical composition can be continued indefinitely as necessary. Alternatively, the treatment can be stopped for a period, and then resumed as necessary on recurrence of symptoms. The effective dosage range of the pharmaceutically acceptable derivatives of fumagillin can be calculated based on the weight of the parent fumagillin to be delivered. If the derivative exhibits activity in itself, the effective dosage can be estimated using the weight of the derivative, or by other means known to those skilled in the art.

Fumagillin or its derivative or pharmaceutically acceptable salt can be administered topically, for example, as a solution, suspension, or ointment. These compositions can be formulated by one of ordinary skill in the art of preparing topical applications using any of a wide variety of carriers or diluents, including but not limited to: a sterile diluent such as water, saline or phosphate buffered saline, fixed oils, polyethylene glycols, glycerine, propylene glycol or other synthetic solvents; antibacterial agents such as benzyl alcohol or methyl parabens; preservatives such as benzalkonium chloride, chlorbutanol, and phenyl mercuric acetate; antioxidants such as ascorbic acid or sodium bisulfite; chelating agents such as ethylenediaminetetraacetic acid; buffers such as acetates, citrates or phosphates, and agents for the adjustment of tonicity such as sodium chloride or dextrose. Agents to adjust pH such as sodium hydroxide, boric acid and sulfuric acid can also be included. Examples of inactive ingredients can include, but are not limited to sodium sulfate, polyvinyl alcohol, polysorbate, mineral oil, corn oil, petrolatum, lanolin alcohol, white petrolatum, cetyl alcohol, glyceryl monostearate, polyoxyl 40 stearate, and cupric sulfate.

The concentration of active compound in the topical carrier or diluent will depend on the absorption and inactivation of the drug as well as other factors known to those of skill in the art. It is to be noted that dosage values will also vary with the severity of the condition to be alleviated. It is to be further understood that for any particular subject, specific dosage regimens should be adjusted over time according to the individual need and the professional judgment of the person administering or supervising the administration of the compositions, and that the concentration ranges set forth herein are exemplary only and are not intended to limit the scope or practice of the claimed composition. The active ingredient may be administered at once, or may be divided into a number of smaller doses to be administered at varying intervals of time.

Fumagillin or its derivative or salt can also be administered in combination or alternation with other topical or systemic pharmaceutical agents, including but not limited to antibiotics, for example, trimethoprin, aminoglycosides, and quinolones; antiviral agents including but not limited to 3'-azido-3'-deoxythymidine (AZT), 2',3'-dideoxycytidine (DDC), 2',3'-dideoxyinosine (DDI), and 2',3'-dideoxy-2',3'-didehydrothymidine (D4T); antifungal agents, antiherpetic agents, wetting agents, other antiparasitic agents.

III. EVALUATION OF ACTIVITY OF FUMAGILLIN AND ITS DERIVATIVES AGAINST MICROSPORIDIAL KERATOCONJUNCTIVITIS AND ACANTHAMOEBA KERATITIS

The activity of fumagillin or its derivative or pharmaceutically acceptable salt against Microsporidial keratoconjunctivitis or Acanthamoeba keratitis can be evaluated in vitro or in vivo, using one or more of the methods set out below.

The activity of the compounds described herein against Microsporidia keratoconjunctivitis can be evaluated in vitro according to any method known to those of ordinary skill in the art. Examples of methods that can be used are described in Shadduck, J. A., et al., "Isolation of a Microsporidian from a Human Patient," *J. Infectious Diseases,* 162 September 1990, and Shadduck, J. A., "Effect of Fumagillin on in vitro Multiplication of *Encephalitozoon cuniculi,*" *J. Protozoology* 27:2, May 1990.

The activity of the compounds described herein against Acanthamoeba keratoconjunctivitis can also be evaluated in vitro according to any method known to those of ordinary skill in the art. An example of a method that can be used is described in Larkin, D. F. P., et al., "Treatment of Acanthamoeba Keratitis with Polyhexamethylene Biguanide," *Ophthalmology,* 99:2, February 1992.

The activity of the compound or its derivative or salt can be evaluated in vivo by administering the compound as described in detail above, followed by evaluation of the progress of the infection with eye scrapings or by monitoring the symptoms of the disease, as described in detail below for two case studies.

EXAMPLE 1

TREATMENT OF MICROSPORIDIAL KERATOCONJUNCTIVITIS WITH FUMAGILLIN

*Encephalitozoon hellem* is a newly described cause of microsporidial keratoconjunctivitis occurring chiefly in patients with a significantly diminished CD4+ T-lymphocyte levels. This disorder is symptomatically disabling and generally recalcitrant to topical antimicrobial therapy. Two homosexual males with *E. hellem* keratoconjunctivitis diagnosed by Gram stain, transmission electron microscopy and specific indirect immunofluorescent assay were treated with topical Fumidil B (fumagillin). Both patients had marked symptomatic improvement with diminished clinical findings. Clinical cure was not achieved in that symptoms and signs of the infection recurred on temporary discontinuation of the drug. Both patients, however, remained symptom free on maintenance levels of topical fumagillin with no evidence of toxic side effects.

Case 1

A 26 year-old homosexual male with AIDS having a several month history of marked light sensitivity, foreign body sensation and ocular redness was examined. His medical history included incidences of Pneumoncystis carnii pneumonia, Mycobacterium avium-M. intracellulare (MAI) complex infection, Cytomegalic virus retinitis in his left eye, chronic diarrhea, persistent dysuria and facial molluscum contagiosum lesions. His CD4+ T-lymphocyte count was $2/mm^3$. The best visual acuity was 20/40 in the right eye with no light perception in the left eye. Bilateral guarding ptosis, tearing, photophobia, conjunctival hyperemia and mild conjunctival follicular hypertrophy were observed. In both eyes, biomicroscopic examination revealed diffuse, coarse white infiltrates and erosions of the corneal epithelium. The lesions were variable in size and shape and seemed confined to the epithelial layer with clinically normal stroma. The larger lesions appeared to develop from the smaller ones. Staining of the corneal surface with 2% fluorescein sodium was irregular and limited chiefly to focci of epithelial erosions. Staining with Rose-Bengal solution was not performed. The remainder of the slit lamp examination was normal. Ophthalmoscopy revealed a normal right ocular fundus, but the left eye had a total retinal detachment secondary to cytomegalovirus retinopathy.

Scrapings from the inferior palpebral conjunctival of both eyes were obtained. Gram stain of a conjunctival smear disclosed numerous Gram-positive ovoid organisms in the cytoplasm of epithelial cells. Transmission electron microscopy of a centrifuged specimen showed numerous spores aggregated within the cytoplasm of conjunctival epithelial cells. These measured $1.2 \times 2.5\mu$ and were encased by a thin electron-dense exospore and a thicker electron lucent endospore. The spores were monokaryotic, and had polar caps and tubules that formed six to seven coils. On the basis of this ultrastructure morphology, a diagnosis of microsporidial keratoconjunctivitis due to Encephalitozoon spp was made. Subsequent confirmation was carried out by a previously described technique wherein a patient's epithelial cells are reacted with rabbit antiserum con-specific for *Encephalitozoon hellem* (Centers for Disease Control-strain: 0291: V213). Spores within the patient's conjunctival epithelial cells reacted intensely with the antiserum provoking a bright, apple green immunofluorescence confirming the presence of *E. hellem*.

Initial attempts at treatment with topical trimethoprim sulfate (0.1%) and polymyxin B sulfate (10,000 units/ml) for two months, followed by topical ciprofloxacin (0.3%) for two weeks, and oral itraconazole (200 mg twice daily) for 10 days resulted in no improvement. The patient continued to be markedly symptomatic and additional therapeutic intervention was attempted sequentially with topical metronidazole (0.5%) for two weeks, and topical thiabendazole suspension (0.4%) for six weeks. There was no resolution of symptoms or clinical findings with any of these regimens.

Fumidil B (fumagillin bicyclohexyl ammonium salt) was obtained from Mid-Continent Agrimarketing (Overland Park, KS) and determined to contain 23 mg of fumagillin/gm of dry powder. Sixty milligrams of Fumidil B was added to 20 ml of sterile saline. The solution was protected from light, filtered with a 0.22μ cellulose acetate filter and transferred to two sterile dropper bottles. Each bottle contained 10 ml of 3 mg/ml Fumidil B which is equivalent to 70 μg/ml of fumagillin. The osmolarity of the treating solutions was 320 mOsm and pH was 6.9. Repeated topical applications of this preparation to six rabbit eyes for five days and to the left eye for three days resulted in no redness or irritation.

The fumagillin preparation was applied to the patient's blind left eye hourly while awake for one week. On reexamination at that time, the symptoms were markedly diminished on the left, worse on the right and the hyperemia and epithelial changes significantly lessened on the left side. Hourly drops were applied topically to both eyes. Within seven days, the patient's symptoms had abated bilaterally with hyperemia and corneal epithelial changes considerably decreased. Scattered intraepithelial opacities were readily observed, but there were no epithelial erosions and the epithelium did not stain with topical fluorescein. Frequency of application was reduced to every 2 hours for one week, then 5 times daily. The patient became asymptomatic with respect to his presenting ocular symptoms, but on slit lamp examination, continued to have scattered irregular white intraepithelial corneal opacities. Vision was 20/20 on the right and unchanged on the left. Gram stain and immunofluorescent assay of the patient's urinary sediment revealed microsporidian spores consistent with *E. hellem*. Following this visit, fumagillin drops were discontinued in the left eye. Within seven days, however, the patient had a recurrence of symptoms and clinical findings for only the left eye. Resumption of medication resulted, again, in marked improvement. The patient remained asymptomatic on topical fumagillin administered five times daily. Sometime later, cytomegalovirus retinopathy resulted in decreased vision in the right eye and fumagillin drops were decreased to twice daily. While useful vision was lost in both eyes, the symptoms of burning and foreign body sensation did not recur and the cornea in each eye revealed persistent, but a markedly decreased number of irregular, white intraepithelial opacities. The patient continued regular twice daily topical fumagillin treatment.

Case 2

A 34 year old homosexual male presented with a two week history of bilateral foreign body sensation, light sensitivity and tearing. He was referred for evaluation of viral conjunctivitis nonresponsive to a topical suspension of neomycin and polymyxin B sulfate and dexamethasone. His medical history included an episode of bacterial pneumonia one year earlier at which time he was diagnosed as serologically positive for Human Immunodeficiency Virus (HIV) infection. On examination, visual acuity was 20/20 on the right eye, and 20/30 on the left eye, with nonspecific conjunctival hyperemia present bilaterally. Slit lamp examination revealed diffuse, whitish erosions involving the corneal epithelium of both eyes. The remainder of the ocular examination including indirect ophthalmoscopy was recorded as normal in both eyes. Conjunctival scrapings were obtained for smear and culture. The culture results were negative, but a Gram-stained smear of conjunctival scrapings demonstrated Gram-positive oval spore-like structures within the cytoplasm of the epithelial cells. A clinical diagnosis of microsporidial keratoconjunctivitis was made. This was subsequently confirmed with transmission electron microscopy and *E. hellem* was identified in the patient's urine by immunofluorescence assay.

Initial treatment with tobramycin-dexamethasone ophthalmic ointment, followed by six weeks of topical metronidazole drops (0.5%) had no effect. A subsequent course of oral itraconazole (100 mg three times daily) for six weeks resulted in some lessening of symptoms and corneal epithelial changes. On discontinuation of the drug, there was complete recurrence of symptoms and findings which persisted in spite of resuming itraconazole orally. Thereafter, propamidine isethionate 0.1% solution (Brolene) was administered topically to both eyes for two weeks with no symptomatic or clinical improvement. On Jun. 15, 1992, topical fumagillin in the form of Fumidil B was initiated with relief of symptoms and remission of clinical findings within three days. During the approximate year of treatment, the patient had a significant decrease in T-lymphocytes bearing the CD4+ receptor (30/m$^3$), and developed anemia on zidovudine, in addition to disseminated MAI complex infection, peripheral neuropathy, renal failure, bilateral cytomegalovirus retinitis and facial molluscum contagiosum lesions. He remained asymptomatic on topical fumagillin several times daily, but scattered, white corneal intraepithelial lesions, without erosion persisted bilaterally.

This invention has been described with reference to its preferred embodiments. Variations and modifications of the method for the treatment of Microsporidia and Acanthamoeba Keratoconjunctivitis, will be obvious to those skilled in the art from the foregoing detailed description of the invention. It is intended that all of these variations and modifications be included within the scope of the appended claims.

I claim:

1. A method for the treatment of microsporidial keratoconjunctivitis that includes the topical administration of an effective amount of a compound of the formula:

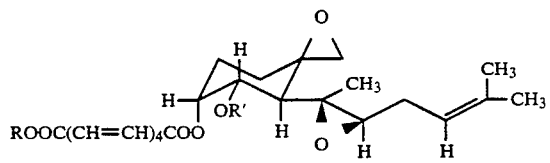

wherein
R is hydrogen; alkyl; phenyl or benzyl, optionally substituted with halogen, $C_1$ to $C_4$ alkyl or $C_1$ to $C_4$ alkoxy, or a mixture thereof; and
R' is hydrogen; alkyl; phenyl or benzyl, optionally substituted with halogen, $C_1$ to $C_4$ alkyl or $C_1$ to $C_4$ alkoxy, or a mixture thereof; or C(O)R" wherein R" is straight, branched, or cyclic $C_1$ to $C_{10}$ alkyl, alkoxyalkyl, aralkyl including benzyl, aryloxyalkyl; phenyl or benzyl, optionally substituted with halogen, $C_1$ to $C_4$ alkyl or $C_1$ to $C_4$ alkoxy, or a mixture thereof; sulfonate ester, the mono, di or triphosphate ester, trityl or monomethoxytrityl; trialkylsilyl, or diphenylmethylsilyl.

2. The method of claim 1, wherein the microsporidia keratoconjunctivitis is caused by *E. cuniculi*.

3. The method of claim 1, wherein the microsporidia keratoconjunctivitis is caused by *E. hellem*.

4. The method of claim 1, wherein the microsporidial keratoconjunctivitis is caused by Nosema sp.

5. The method of claim 1, wherein R is H and R' is methyl.

6. The method of claim 1, wherein the compound is administered as a pharmaceutically acceptable salt.

7. The method of claim 6, wherein the salt is the bicyclohexyl ammonium salt of the compound.

8. The method of claim 1, wherein the compound is administered in a dosage concentration of between 50 µg/ml and 10 mg/ml.

9. The method of claim 1, wherein the compound is administered between once and four times daily.

10. A method for the treatment of Acanthamoeba keratoconjunctivitis that includes the topical administration of an effective amount of a compound of the formula:

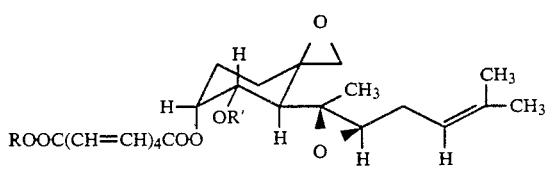

wherein
R is hydrogen; alkyl; phenyl or benzyl optionally substituted with halogen, $C_1$ to $C_4$ alkyl or $C_1$ to $C_4$ alkoxy, or a mixture thereof; and
R' is hydrogen; alkyl; phenyl or benzyl, optionally substituted with halogen, $C_1$ to $C_4$ alkyl or $C_1$ to $C_4$ alkoxy, or a mixture thereof; or C(O)R" wherein R" is straight, branched, or cyclic $C_1$ to $C_{10}$ alkyl, alkoxyalkyl, aralkyl including benzyl, aryloxyalkyl; phenyl or benzyl, optionally substituted with halogen, $C_1$ to $C_4$ alkyl or $C_1$ to $C_4$ alkoxy, or a mixture thereof; sulfonate ester, the mono, di or triphosphate ester, trityl or monomethoxytrityl; trialkylsilyl, or diphenylmethylsilyl.

11. The method of claim 10, wherein R is H and R' is methyl.

12. The method of claim 10, wherein the compound is administered as a pharmaceutically acceptable salt.

13. The method of claim 12, wherein the salt is the bicyclohexyl ammonium salt of the compound.

14. The method of claim 10, wherein the compound is administered in a dosage concentration of between 50 µg/ml and 10 mg/ml.

15. The method of claim 10, wherein the compound is administered between once and four times daily.

16. A topical composition for the treatment of Microsporidial Keratoconjunctivitis or Acanthamoeba Keratitis that includes an effective amount of a compound of the formula:

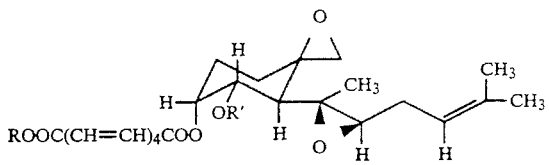

wherein
R is hydrogen; alkyl; phenyl or benzyl optionally substituted with halogen, $C_1$ to $C_4$ alkyl or $C_1$ to $C_4$ alkoxy, or a mixture thereof; and
R' is hydrogen; alkyl; phenyl or benzyl, optionally substituted with halogen, $C_1$ to $C_4$ alkyl or $C_1$ to $C_4$ alkoxy, or a mixture thereof; or C(O)R" wherein R" is straight, branched, or cyclic $C_1$ to $C_{10}$ alkyl, alkoxyalkyl, aralkyl including benzyl, aryloxyalkyl; phenyl or benzyl, optionally substituted with halogen, $C_1$ to $C_4$ alkyl or $C_1$ to $C_4$ alkoxy, or a mixture thereof; sulfonate ester, the mono, di or triphosphate ester, trityl or monomethoxytrityl; trialkylsilyl, or diphenylmethylsilyl;
or its pharmaceutically acceptable salt, in a pharmaceutically acceptable carrier or diluent.

17. The composition of claim 16, wherein the composition includes between approximately 50 µg/ml and 10 mg/ml of active compound.

18. The composition of claim 16, wherein the composition is in the form of a solution.

19. The composition of claim 16, wherein the composition is in the form of a suspension.

20. The composition of claim 16, wherein the composition is in the form of an ointment.

21. The composition of claim 16, wherein the composition comprises a material selected from the group consisting of sterile water, saline or phosphate buffered saline, fixed oils, polyethylene glycols, glycerine, polyvinyl alcohol, polysorbate, mineral oil, corn oil, petrolatum, lanolin alcohol, white petrolatum, cetyl alcohol, glyceryl monostearate, polyoxyl 40 stearate and propylene glycol.

22. The composition of claim 16, wherein the compound is in the form of a pharmaceutically acceptable salt.

23. The composition of claim 22, wherein the salt is water soluble.

24. The composition of claim 23, wherein the compound is in the form of a bicyclohexyl ammonium salt.

* * * * *